United States Patent [19]
Klauser et al.

[11] Patent Number: 6,040,141
[45] Date of Patent: Mar. 21, 2000

[54] BACTERIA FOR PREPARING STABLE FUSION PROTEINS AND METHODS FOR DETECTING THE SAME

[75] Inventors: Thomas Klauser, Fellbach; Joachim Kramer, Rottenburg; Thomas F. Meyer; Johannes Pohlner, both of Tübingen, all of Germany

[73] Assignee: Max-Planck-Gesellschaft zur Forderung der Wissenschaften e.V., Berlin, Germany

[21] Appl. No.: 08/666,354

[22] PCT Filed: Dec. 22, 1994

[86] PCT No.: PCT/EP94/04286

§ 371 Date: Sep. 23, 1996

§ 102(e) Date: Sep. 23, 1996

[87] PCT Pub. No.: WO95/17509

PCT Pub. Date: Jun. 29, 1995

[30] Foreign Application Priority Data

Dec. 23, 1993 [DE] Germany ............... 43 44 350

[51] Int. Cl.$^7$ .............. C12Q 1/68; C12P 21/00; C12N 1/21; C12N 5/11
[52] U.S. Cl. .............. 435/6; 435/7.1; 435/69.1; 435/91.41; 435/252.3; 435/252.33; 536/23.1; 536/23.4; 536/23.7
[58] Field of Search .............. 435/252.33, 69.1, 435/6, 7.1, 91.41, 252.3; 536/23.1, 23.4, 23.7

Primary Examiner—John S. Brusca
Attorney, Agent, or Firm—Birch, Stewart, Kolasch & Birch, LLP

[57] ABSTRACT

The present invention relates to bacteria for preparing stable fusion proteins from a carrier protein and a passenger protein, the bacteria possessing the genetic marker fpt. This genetic marker permits the improved preparation of protein fusions having a destabilizing effect on bacteria. The present invention in particular relates to bacteria for preparing fusion proteins, the bacteria stably presenting the fusion proteins on their surface and possessing the markers ompT$^-$ and dsbA$^-$ in addition to the genetic marker fpt. Moreover, the present invention relates to the identification of bacteria, which present heterologous proteins having an affinity to a binding partner on its surface and methods for constructing vectors encoding these proteins. Finally, the present invention also relates to bacteria which stably present at least one fusion protein on their surface and possess the genetic markers fpt, ompT$^-$ and dsbA$^-$, and their use for instance for diagnostic purposes.

24 Claims, 11 Drawing Sheets

BACTERIA FOR PREPARING STABLE FUSION PROTEINS AND METHODS FOR DETECTING THE SAME

The present invention relates to bacteria for preparing stable fusion proteins from a carrier protein and a passenger protein, the bacteria possessing the genetic marker fpt. This genetic marker permits the improved preparation of protein fusions having a destabilizing effect on bacteria. The present invention in particular relates to bacteria for preparing fusion proteins, the bacteria stably presenting the fusion proteins on their surface and possessing the markers ompT⁻ and dsbA⁻ in addition to the genetic marker fpt. Moreover, the present invention relates to the identification of bacteria, which surface-present heterologous proteins having an affinity to a binding partner and methods for constructing vectors encoding these proteins. Finally, the present invention also relates to bacteria which stably present at least one fusion protein on their surface and possess the genetic markers fpt, ompT⁻ and dsbA⁻, and their use for instance for diagnostic purposes. For example, the method of the invention in particular permits the formation of protein fusions which are composed of portions of heavy and light antibody domains and portions of the Igaβ transport protein, and their export through the bacterial cell envelope. In a specific embodiment, recombinant antibody fusions with binding activity can be presented on the bacterial surface of *Escherichia coli* cells.

Specific interactions between receptor molecules and ligands constitute a basic phenomenon of biological systems. Even extremely complex processes in highly developed organisms can be reduced to simple molecular interactions and can be analyzed and effectively influenced on this level. The specificity of such interactions is expressed in the affinity between the biomolecules involved, i.e. the binding forces between the receptors and the ligands.

In order for biological processes to be specifically investigated and manipulated, it is necessary to prepare analogues possessing defined binding properties and being suitable for the most different receptors and ligands. For this purpose, artificial systems are developed permitting the simple preparation of a multitude of receptor or ligand structures on the one hand and the selection and propagation of molecules possessing defined binding properties on the other hand. Such systems, in which biomolecules having defined properties can be obtained by evolution-like mechanisms can be realized in different ways. According to one strategy which closely adheres to the principles of living systems, for instance the principle of clonal selection in the immune system of mammals, a biomolecule presented on the cell surface is coupled with the propagation apparatus of living cells in the form of the encoding genetic information. The cells do not only assume the function of producing structurally variable biomolecules but also enable the selection of suitable molecules by presenting the biomolecules on their surface, and in the process of their cell division also enable the propagation of the underlying genetic information.

The physical basis of such a system is formed by both the producer cells and the genetic information, determining the blueprint of a biomolecule. The producer cells have to be capable of propagation, and at the same time must be capable of expressing heterologous genetic information and presenting the corresponding biomolecules accessibly on their surface. Ideally, they are easy to genetically manipulate, possess physico-chemical and genetic stability and are undemanding in respect of their growth conditions. A suitable microorganism meeting these requirements is *Escherichia coli*. Suitable biomolecules are preferably proteins. The underlying genetic information can extend from a few codons up to several genes, depending on whether a short peptide, a protein or a receptor consisting of several protein molecules is encoded. With the use of conventional methods of molecular biology it is possible to produce a multitude of protein variants on the genetic level and to express the heterologous information after its incorporation into the producer cell.

As explained above, an essential prerequisite for the functioning of a cellular selection system is the presentation of the corresponding protein molecules on the cell surface. The accessibility to potential binding partners must be ensured and the binding properties must not be affected by cellular determinants. In *Escherichia coli*, different systems for presenting recombinant proteins have been worked out. The main feature of these systems is the use of protein fusions and the gene fusions underlying them. The fusions contain carrier protein portions, apart from the protein portions containing the corresponding receptor or ligand structures. The carrier portions enable the export of the protein fusion from the cytoplasm through the two cell membranes of *E. coli* and their anchorage in the outer membrane.

The expression of gene fusions in recombinant cells, such as *E. Coli*, often involves problems, and in some cases is impossible. In this connection, two reasons can be pointed out: On the one hand, the formation of protein fusions especially in connection with membrane transport processes can affect the viability of the cells and their ability to propagate. As a result, mutants are selected from a population of recombinant cells which show no or only a reduced expression of gene fusions. The fusions of portions of heavy immunoglobulin chains with carrier protein portions from the protein A represent a well known example of this problem (Plückthun et al., Cold Spring Harbor Symposia 52 (1987) 105–112). Another problem often to be found is the instability of the protein fusions once formed. In this connection, in particular the sensitivity of recombinant proteins vis-à-vis proteases and the artificial folding properties of such protein fusions are of importance. For such critical protein fusions to be nevertheless produced, it is necessary to adapt the genetic background of the producer cells to the corresponding requirements by effecting suitable changes. The use of cells with reduced protease activity is only one example.

Different systems have been used for presenting recombinant proteins on the cell surface. A signal peptide at the amino end enables the transport of protein fusions through the inner membrane, while other portions are responsible for the incorporation and anchorage in the outer membrane. In many cases, proteins of the outer membrane of *E. coli* can be used as carrier portions, e.g. LamB (Charbit et al., EMBO J. 5 (1986), 3029–3037), PhoE (Agterberg et al., Gene 88 (1990), 37–45) and OmpA (R. Freudl, Gene 82 (1989) 229–236). In these cases, the possible applications are, however, very limited, as additional protein sequences can be integrated only into the loops exposed on the surface. On the one hand, this is a limitation of the length of additional protein sequences, and on the other hand the latter are framed on both sides by carrier protein sequences, whereby both the amino and the carboxy termini of these sequences are topologically fixed. It is true that fusions with portions of the peptidoglycan-associated lipoprotein (PAL) enable transport to the outer membrane. However, a presentation of native protein sequences on the surface of E. coli is not thereby achieved (Fuchs et al, Bio/Technology 9 (1991), 1369–1372). A system which evidently allows larger proteins, too, to be surface-presented in E. coli is based on fusions with portions from Lpp and ompA. Protein sequences which are attached to the carboxy terminus of such a Lpp-OmpA fusion are accessible on the surface of recombinant E. coli cells after their export (Francisco et al., Proc. Natl. Acad. Sci. USA 89 (1992), 2713–2717). When the amino end of the protein sequences to be presented is topologically fixed to the membrane-anchoring OmpA sequence, this can have an adverse effect, especially in cases in which a free amino end is necessary for functional reasons.

The fusions with the transport domain of the IgA-protease precursor Igaβ occupy a special place in the event that E. coli are used to present proteins (Klauser et al., EMBO J. 9 (1990), 1991–1999). This transport system allows even large passenger proteins to be transported to the surface of E. coli cells, if they are fused at their amino terminus with a signal peptide and at their carboxy terminus with the Igaβ-domain or parts of this domain. In contrast to the above-mentioned Lpp-OmpA-system, the proteins presented by means of Igaβ (membrane anchor) have a free amino end, while the carboxy terminus is linked to the membrane anchor (Igaβ). An important factor which influences the anchorage of Igaβ-fusions on the surface of E. coli cells is the OmpT-protease, which is a protein localized in the outer membrane. Its activity directed to the surface of the bacteria leads to the cleavage of Igaβ fusions and thus to the decoupling of surface-presented passenger proteins (Klauser et al., EMBO J. 11 (1992), 2327–2335). As a result of this activity, the binding properties of the passenger proteins are prevented from physically coupling to the propagation apparatus of the cells. Thus, a selection of the producer cells is precluded. This effect can be circumvented by the use of OmpT-negative E. coli host cells.

Processes for the surface-presentation of proteins in E. coli are of special importance in the search and manipulation of polypeptides that lend themselves to therapeutical and diagnostic uses. The extensive findings in immunology and cellular biology have led to the identification of many proteins as potential candidates. The immunoglobulins represent a protein family which receives much attention in this connection. The preparation of immunoglobulins by recombinant methods has become increasingly important in recent years. In this connection, the possibility of establishing entire antibody libraries in microorganisms involving the possibility of newly generating, modifying, selecting and propagating suitable antibodies, is of interest.

At the present stage of research, the presentation of antibody fragments on the surface of filamentous bacteriophages (fd) is the best developed system. In this system, the antibody fragments are present in the form of protein fusions with the phage envelope proteins g3p or g8p. In both cases, it is possible to select from a recombinant phage population phages that possess the desired specificity provided by the surface-presented antibody fragment (Winter and Milstein, Nature 349 (1991), 293–299). A decisive disadvantage of using phages as carriers of antibody fragments as compared to bacterial cells is the fact that phages are not capable of self-replication but require host bacteria which ensure their propagation. The preparation of phages possessing the desired binding properties therefore requires expensive cycles of selection and infection (phage propagation). This drawback is not encountered when using whole bacterial cells as carriers of recombinant antibody fusions. On the other hand, a method for identifying recombinant antibodies which is based on the lambda phage does not permit the selection of specificities but requires expensive screening procedures (Lerner et al., Science 252 (1991), 659–667). There is hardly another system as well suited as the Igaβ-domain or C-terminal portions of this domain to serve as a membrane anchor for the presentation of recombinant antibody domains on the surface of gram negative bacteria, such as E. coli, Salmonella and Neisseria. Compared to the above-described phage systems, a bacterial system is distinguished by functional, surface-presented antibodies directly coupled to the propagation apparatus of living cells. On the bacterial level, there largely exists the possibility of obtaining larger amounts of functional antibody fragments, apart from the possibility of direct selection and manipulation. The antibody fragment can either be obtained from the cytoplasm in the form of inclusion bodies or from the periplasm in the form of a soluble protein. The antibody fragments existing in the periplasm are correctly folded and therefore biologically active and can be purified directly from fractions of the periplasm. The inclusion bodies existing in the cytoplasm consist of denatured antibody fragments which possess no biological activity. The latter is achieved after simple purification of the antibody fragments by denaturation and renaturation. The recombinant antibody fragments are capable of binding an antigen with an affinity equivalent to that of the native antibody molecule.

However, after transformation with plasmids, which for instance express a VH-Igaβ fusion, these plasmids are found to be highly unstable and to lyse the recombinant bacteria in the host strains. An identical phenotype has been described by another work team in connection with the export of a fusion between an VH domain and the protein A of *Staphylococcus aureus*. This phenomenon is apparently elicited by the signal peptide-dependent, disturbed secretion of VH domains that are fused to an exoprotein determinant.

Hence, the present invention is based on the technical problem of providing bacteria not suffering from these drawbacks that is to say which generally have an increased stability in the expression of a fusion protein formed from a carrier protein and a passenger protein. This technical problem is solved by the provision of the embodiments characterized in the claims. Surprisingly, it has been found that a possibility of preventing the cell-destabilizing activity of fusion proteins is the use of particular host cells possessing the genetic marker fpt.

Thus, the invention relates to a bacterium for preparing at least one stable fusion protein from a carrier protein and a passenger protein, the bacterium possessing the genetic marker fpt.

According to the invention, the abbreviation fpt denotes a genetically determined feature of *E. coli,* resulting in the tolerance of bacterial instability occasionally appearing in the expression of exported fusion proteins. Said marker is a mutation localized between the 85 and 89 minute positions of the gene map of the *E. coli* genome. An example of the fpt markerlies within that portion of the genome of *E. coli* JCB571 bearing both of the markers dsbA::Kan and zih12::Tn10. The genetic marker fpt can be used to prepare bacteria that are tolerant towards fusion proteins.

According to the invention, the term "carrier protein" denotes amino acid sequences within a fusion protein which do not belong to the passenger protein and are important for the localization and stability of the fusion proteins in the bacteria. In the case of fusion proteins which are presented on the bacterial surface, the carrier protein portions contain a signal peptide at the amino end of the fusions and the Igaβ-transport domain at the carboxy terminus of the fusions. In the case of fusion proteins which are transported into the periplasm, the carrier protein portions contain a signal peptide at the amino end of the fusions.

According to the invention, the term "passenger protein" denotes amino acid sequences within a fusion protein which do not belong to the carrier protein. In the case of fusion proteins which are presented on the bacterial surface, the passenger protein portions contain the sequences that interact with the binding partners.

The preparation of an optimized *E. coli* host strain enabling a stable surface-presentation of fusion proteins requires the introduction of additional genetic changes, apart from the existence of this mutation. In tests for secretion of Igaβ-fusion proteins in *E. coli* it has been shown that the Igaβ domain in the outer membrane is cleaved by OmpT protease and thus the passenger protein is decoupled from the membrane anchor Igaβ. Moreover, the translocation of passenger proteins to the cellular surface is possible in their unfolded configuration only. If the Igaβ-mediated secretion of variable antibody domain occurs in *E. coli* K12 wild type strains or in *E. coli* (ompT⁻), then the immunoglobulin portions of unspecific periplasmic proteases undergo degradation. The reason therefor is that the periplasmic disulfide oxidoreductase DsbA forms intramolecular disulfide bridges in the passenger proteins. This blockage of the translocation of passenger proteins through the outer membrane is not found in cells carrying a mutation in the dsbA gene.

In a preferred embodiment, the present invention therefore relates to a bacterium which possesses the genetic marker fpt, stably presents the fusion protein on its surface, is gram negative and additionally possesses the genetic markers ompT⁻ and dsbA⁻.

According to the invention, the phrase "presented on the surface" denotes the localization of a fusion protein or the passenger protein on the side of the outer bacterial membrane facing the medium. In intact gram negative bacteria, passenger proteins presented on the surface are freely accessible to binding partners.

The abbreviation ompT⁻ denotes a genetic change in *E. coli* cells which leads to a deficiency in the proteolytic activity of the protease OmpT.

The abbreviation dsbA⁻ denotes a genetic change in *E. coli* cells leading to a deficiency in the activity of the periplasmic oxidoreductase DsbA. According to the invention, the term dsbA⁻ is to be understood to include not only a deficiency in activity caused by a genetic change of the very oxidoreductase DsbA, but also by other factors which indirectly inhibit the activity of said oxidoreductase.

According to the invention, the mutations of the three aforementioned genes in the chromosome of a bacterial cell are combined in *E. coli* UT5600 (ompT⁻). The very *E. coli* UT5600 is mutated in one gene (ompT). This transfer of the mutation in the dsbA gene to *E. coli* UT5600 was performed from *E. coli* JCB571 (dsbA::Kan; zih12::Tn10) by means of phage p1-transduction. Positive transductants were selected for the cotransduction of a transposon Tn10 insertion near the dsbA gene locus. In this manner, the property determined by the adjacent DNA sections which enables an *E. coli* cell to stably produce for instance VH-Igaβ fusions was also transferred.

In another preferred embodiment, the bacterium is used for the preparation of a fusion protein wherein the carrier protein contained in the fusion protein contains the Igaβ protein or a fragment thereof enabling the secretion of the fusion protein.

The abbreviation "Igaβ" denotes the transport domain localized at the carboxy terminus of the Neisseria IgA-protease precursor protein. Said domain mediates the transport of amino terminally coupled proteins from the periplasm of gram negative bacteria through the outer membrane.

In a particularly preferred embodiment, the passenger protein prepared by the bacterium of the invention is a protein having an affinity to the binding partner, or is an antibody, an antigen-binding domain of an antibody, an antigen, a protein having enzymatic activity, an inhibitor, a receptor, a ligand or a nucleic acid binding protein.

According to the invention the term "binding partner" is a molecule, a chemical compound or a macromolecule. Binding partners may be freely soluble, bound to a template or associated with a biological membrane.

According to the invention, the term "antigen-binding domain" denotes at least that portion of an antibody molecule which is sufficient to specifically bind an antigen.

The method described herein enables the stable production and presentation of immunoglobulin domains on the surface of gram negative bacteria. The method can be practiced in two different ways. The export of the variable antibody domains occurs either in the form of a monomeric ("single-chain Fv") scFv-Igaβ fusion in which the domains VL and VH are covalently linked by a short peptide (for instance a $(Gly_4 Ser)_3$-linker) or in the form of two separate VL- and VH-Igaβ fusions within one bacterial cell. In the latter case, the antibody portions of both fusions anneal on the cell surface to form a functional Fv-fragment. The use of different *E. coli* K12 strains together with the VL- and scFv-Igaβ constructs led to stable transformants.

In the most preferred embodiment, the bacterium used for preparing the fusion proteins is the strain *E. coli* JK 321. This strain was deposited at the DSM (Deutsche Sammlung von Mikroorganismen, 38124 Braunschweig, Mascheroder Weg 1b, Deutschland) (accession number DSM 8860) on Dec. 22, 1993 in accordance with the provisions of the Budapest Treaty.

Another object of the present invention is the provision of the genetic marker fpt to generate a bacterial tolerance towards fusion proteins.

The development of strains containing this marker which enables the stable surface-exposure of fusion proteins offers quite some possibilities of use. For instance, the selection of a particular *E. coli* clone possessing particular properties from an immunoglobulin-Igaβ library using any antigen is conceivable.

It is therefore another object of the present invention to provide a method for identifying bacteria which stably present on their surface proteins having an affinity to a binding partner, the method comprising the following steps:

(a) constructing at least one vector containing at least one DNA sequence encoding a fusion protein which is made from a carrier protein and a passenger protein and can be stably presented on the surface of the bacteria;

(b) introducing the vector into said bacteria;

(c) culturing the bacteria of step (b) in such a way that the bacteria of the resulting culture stably present the fusion protein(s) on their surface;

(d) isolating bacteria which present the desired fusion protein(s) on their surface.

The presentation of more than one fusion protein on the cellular surface may be desirable for instance in cases where individual chains of multimeric proteins are expressed separately which then anneal on the cellular surface to form a functional complex.

In a preferred embodiment of this method, the construction of the vector in step (a) is performed using a library of DNA sequences in which the corresponding DNA-sequences encode variants of the passenger protein(s) or variants of the carrier protein(s).

According to the invention, the term "variant of passenger proteins" denotes amino acid sequences deviating from passenger proteins in binding properties modified in respect of a binding partner.

According to the invention, the term "variant of carrier proteins" denotes carrier proteins whose amino acid sequence is modified and which have modified transport properties in respect of the passenger proteins coupled to them.

In the construction of variants of passenger proteins, an antibody fragment of given specificity could for instance be optimized by site-directed mutagenesis to become useful for a particular type of application. The continuous cultivation of *E. coli* cultures is a possibility to achieve an evolution-like adaptation to an external factor through site-non-directed mutagenesis. Moreover, this method allows not only antibody fusions to be processed but also enzymatic activities to be presented, selected and modified. The production of variants of the carrier protein can bring about a better adaptation to a given passenger protein or its variants which can facilitate the secretion of the fusion protein.

In another preferred embodiment of the instant method, the bacterium is cultured in step (c) under conditions causing the DNA sequence encoding the fusion protein(s) to undergo mutation, with the result that the bacteria of the resulting culture present variants of the fusion protein(s) on their surface.

According to the invention, the term "mutation conditions" denotes culturing conditions under which the rate of mutation in bacteria cultures is increased on account of the addition of chemical substances and/or the action of ionizing irradiation.

In a preferred embodiment of this method, the carrier protein contained in the fusion protein contains the Igaβ-protein or a fragment thereof which facilitates the secretion of the fusion protein.

In another, particularly preferred embodiment of this method, the protein having an affinity to a binding partner is an antibody or an antigen-binding domain of an antibody, an antigen, a protein having an enzymatic activity, an inhibitor, a receptor, a ligand or a nucleic acid binding protein.

Finally, in another, particularly preferred embodiment of this method, the bacteria stably presenting the desired fusion protein on their surface can be isolated by interaction with the template-bound binding partner of the passenger protein, or by interaction with a fluorescence-labelled binding partner, or by interaction with the magnetic particle-bound binding partner of the passenger protein.

Another object of the present invention is the provision of gram negative bacteria which stably present at least one fusion protein on their surface and possess the genetic markers fpt, ompT$^-$ and dsbA$^-$.

A preferred embodiment relates to bacteria, wherein the carrier protein contained in the fusion protein contains the Igaβ protein or a fragment thereof which facilitates the secretion of the fusion protein, and/or the passenger protein is a protein possessing an affinity to a binding partner, or is an antibody, an antigen-binding domain of an antibody, an antigen, a protein with an enzymatic activity, an inhibitor, a receptor, a ligand or a nucleic acid-binding protein.

Finally, it is another object of the present invention to use these bacteria for diagnostic purposes, for the preparation of proteins having an affinity to a binding partner, the preparation of detergents or the utilization of raw materials, food processing or the decomposition of or enrichment with pollutants.

The bacteria of the invention, presenting specific antibody fragments, can, for instance, be used to obtain said antibody fragments, and, optionally after purification, the latter can then be used for diagnostic or therapeutic purposes. Recombinant antibody fragments which for instance recognize specific surface structures of tumor cells can be used for therapeutic applications together with a radionuclide or an effective toxin. Binding specificities selected with the use of the inventive method can be integrated (humanized) into human immunoglobulin chains by a genetechnological transfer of the CDR (complementary determining regions) regions and can be used to treat diseases.

DESCRIPTION OF THE FIGURES

FIG. 2A: The plasmid pJK78 was formed by incorporating a DNA fragment containing the VL-gene fragment of a monoclonal antibody into the NdeI/EcoRI-vector fragment of the plasmid pTK59. First, the VL-gene fragment was produced using the oligonucleotides JK08 and JK14 (Table 1) in a polymerase chain reaction and cloned into the pCR1000 vector (pJK56). The corresponding DNA-fragment of the VL-gene was processed at the NdeI and EcoRI restriction sites introduced by the oligonucleotides at the 5' and 3' ends and was ligated with the NdeI/EcoRI-vector fragment of the plasmid pTK59. The resulting plasmid was termed pJK78.

FIG. 2B: The exchange of the gene of the b-lactamase (bla) and the ColEl replication origin on the plasmid pJK78 was performed in two steps. In the first step, the gene of the chloramphenicol acetyl transferase (cat) of the plasmid pACYC184 was amplified by PCR using the oligonucleotides JK32 and JK33 (Table 1). The resulting PCR fragment was cloned into the pJK78-vector fragment cut with HindIII. The plasmid pJK250 thus obtained is distinguished by the presence of two resistance genes (bla and cat) and the ColEl replication origin. By restriction with ClaI and NheI, the vector fragment (bla and ColEl) was deleted from pJK250 and substituted with a ClaI/NheI fragment (p15A-origin) from the plasmid pACYC184. The resulting plasmid pJK257 encodes a VL-igaβ fusion and permits its coexpression together with the plasmid pJK165 (VH-igaβ) within E. coli JK321 cells.

Recombinant E. coli JK321 cells which express the gene fusions of ctxB-igaβ (plasmid pTK59) with VH- and VL-igaβ (plasmids pJK165 and pJK257) were cultured in an LB-medium, pH=8.5, in the presence of 2-mercapto ethanol (7.5 mM) and the correspondingly needed antibiotics at 28° C. overnight. After being washed once in PBS, the bacteria were incubated in PBS/BSA (1%) in order to saturate unspecific binding sites on the cellular surface. After addition of the specific antigen (a-protein, 100 ng/ml) the cell suspension was placed into a rotating incubator for a further 30 minutes and then washed in PBS once. Surface-bound antigen was fixed with paraformaldehyde (1%)/glutardialdehyde (0.5%) and detected with antigen-specific, polyclonal serum (anti-Fp80) and FITC-coupled mouse-anti-rabbit-IgG serum.

Figure 6:
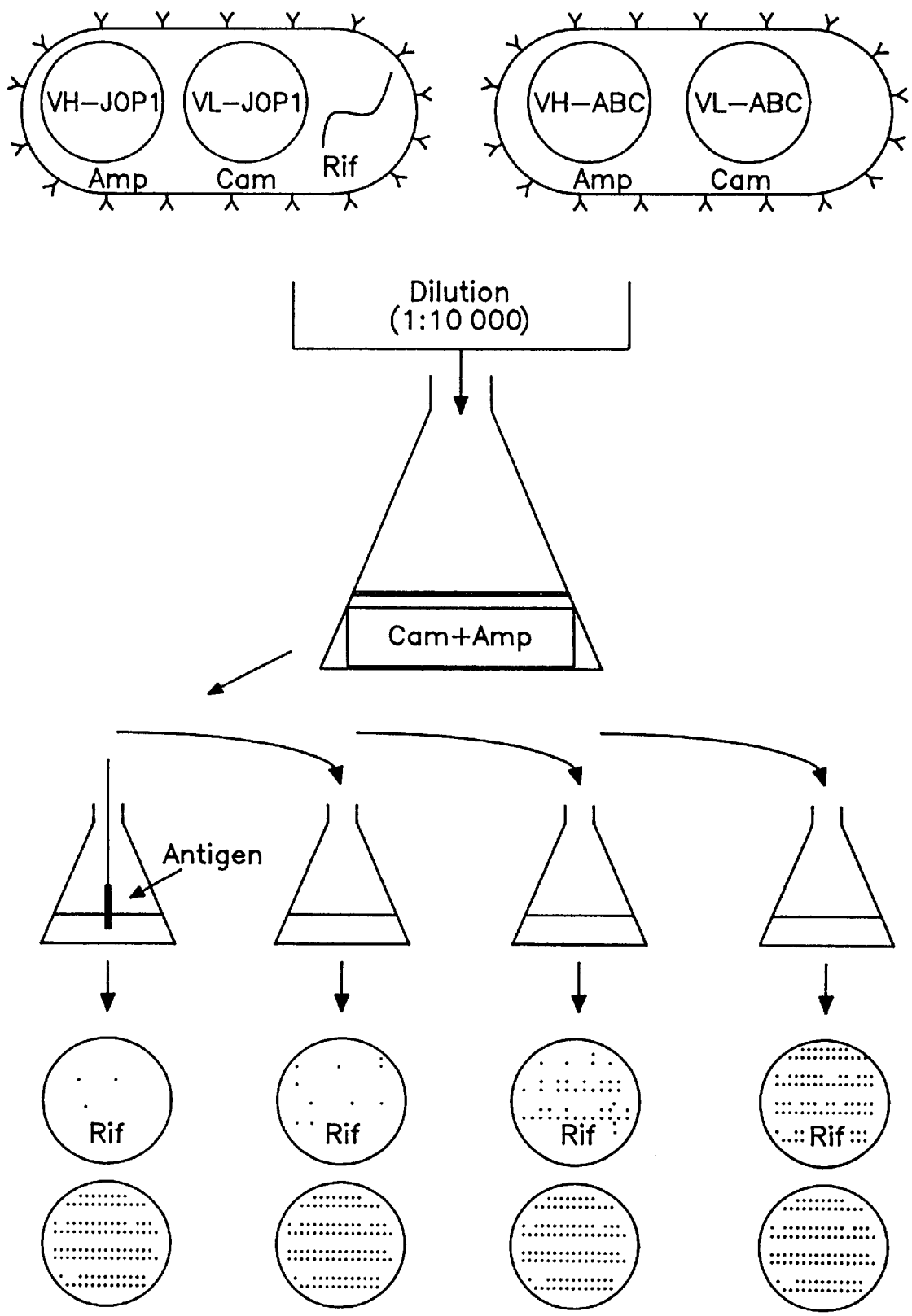

FIG. 6: Schematic representation of method for detecting antibody-presenting E. coli JK321. In order to allow monitoring the enrichment of specific, VL-/VH-Igaβ producing E. coli JK321 cells by means of the specific antigen, these recombinant bacteria carry a rifampicin marker (rif) in their chromosome, which enables them to selectively grow on the nutrient medium plates (rif). By contrast, the control cells only grow on rif-free medium. Thus, the ratio of rif-resistent to rif-sensitive bacteria colonies allows the selective enrichment of the specific VL-/VH-Igaβ coexpressing JK321 cells to be determined. In the scheme, the specific rif-resistent E.

coli JK321 are diluted in a ratio of 1:1000 relative to the control cells E. coli UT5600 which produce VL-/VH-Igaβ fusions of a different antigen specificity and are cultured in the nutrient medium at the beginning of selection. Subsequently, the specific E. coli JK321 are fished out from the cell suspension by means of an immobilized antigen, transferred to fresh nutrient medium and cultured again. This procedure is repeated several times and each time an aliquot is plated onto the nutrient medium plates with and without rifampicin. In the course of this procedure, a continuous increase in the rif-resistant bacteria clones as compared to rif-sensitive ones should be found.

Figure 7:
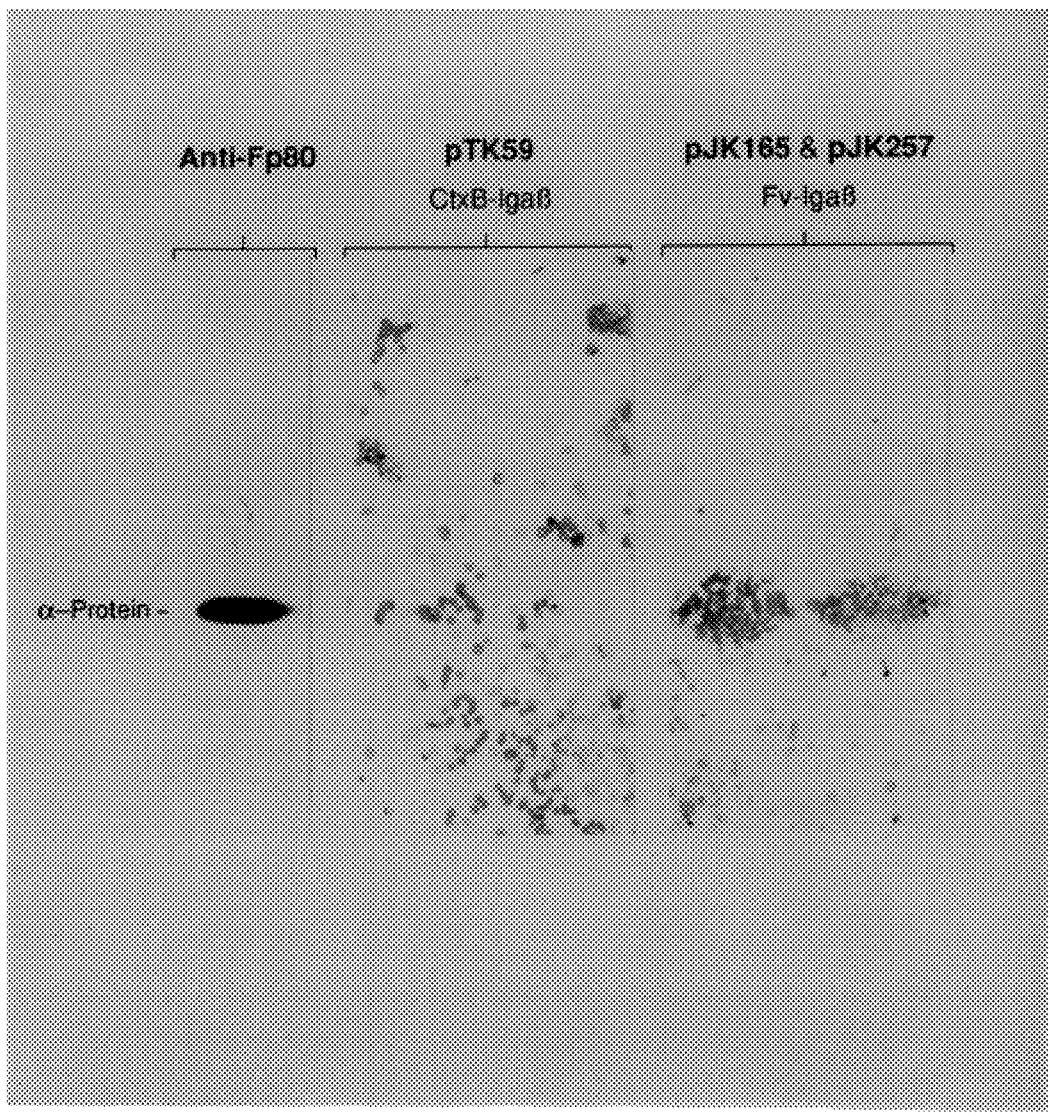

FIG. 7: Selective enrichment of VL-/VH-Igaβ coexpressing E. coli JK321 by antigen-labelled nitrocellulose. After separation of a-protein (about 10 ng/lane) by SDS-PAGE, the antigen was subsequently blotted onto nitrocellulose. A nitrocellulose strip immunoblot was developed with anti-Fp80 in order to make the precise position of the a-protein band visible. For performing the binding experiments, the E. coli strains UT5600 (pTK59; Rif$^S$), JK321 (pTK59; Rif$^R$) and JK321 (pJK165/pJK257; Rif$^R$) were cultured overnight as liquid cultures. At an O.D.$_{600}$ of 0.8, the two recombinant, rif-resistant JK321 strains were diluted in a ratio of about 1:2000 relative to the rif-sensitive strain UT5600 (pTK59). After incubation of the bacterial suspension in PBS/BSA (1%) for 30 minutes, 1 ml thereof was placed into 15 ml of PBS and into an empty petri dish together with a nitrocellulose strip. After incubation at room temperature for 30 minutes under slight agitation, three washings with PBS (20 ml) were carried out, and subsequently the nitrocellulose was incubated on rif-bearing nutrient medium plates.

The following examples illustrate the invention

EXAMPLE 1

Preparation of the E. coli strain JK321 by transfer of a stability determinant using P1-phage transduction.

For Igaβ-domain-mediated presentation of variable antibody fragments or other pharmacologically relevant proteins on the cellular surface of E. coli, it is necessary to inactivate the genes of several enzymes which are localized in the periplasm and the outer membrane. In this connection, particularly the periplasmic disulfide oxidoreductase (DsbA) (Bardwell et al, Cell 67 (1991), 581–589) or an outer membrane protease (OmpT) (Earhart et al., FEMS Microbiol. Let 6 (1979) 277–280); Grodberg and Dunn, J. Bacteriol. 171 (1989), 2903–2905) should be mentioned. Apart from the inactivation of these two factors, it is, however, necessary especially for the Igaβ-mediated surface-exposure of the variable heavy antibody domain (VH) to additionally eliminate another gene in the E. coli genome. Otherwise, this VH-Igaβ fusion protein has a cytotoxic effect on the E. coli K12 host cells. In the preparation of the E. coli strain JK321, one section of the genome of an E. coli strain (JCB571) (Bardwell loc. cit.) carrying a mutation in a gene not known in more detail was transferred to another E. coli strain (UT5600) (Earhart, loc. cit.). Only the introduction of this mutation into the genome of E. coli K12 enables the stable production of VH-Igaβ fusion proteins in these genetically modified host cells.

A method of exchanging larger fragments of the chromosomal DNA between two E. coli strains is the transduction by means of P1-phages which is normally used for mapping

TABLE 1

DNA sequences of the oligonucleotides used

| Name | Purpose of use[a] | lengths (bp) and order of sequence (5' after 3') | |
|---|---|---|---|
| JK008 (SEQ. ID. NO.:1) | PCR (−) | 35 | GCAGCAGAATTCCGTTTCAGCTCCAGCTTG GTCCC |
| JK009 (SEQ. ID. NO.:2) | PCR (−) | 44 | GCAGCAGAATTCGCAGAGACAGTGACAGT (G/A)GTGCCTTGGCCCCA |
| JK014 (SEQ. ID. NO.:3) | PCR (+) | 44 | GGTTATGCATATGCACATGGAACACCTGAT (A/G)TTGTGAT(G/A)ACCCA |
| JK017 (SEQ. ID. NO.:4) | PCR (+) | 50 | GGTTATGCATATGCACATGGAACACCTCAG GTCCAACTTCTCGAGTCAGG |
| JK020 (SEQ. ID. NO.:5) | PCR (+) | 44 | GCAGCAATCGATGAGTAATACTTGCGCGCC AAGGGTGCTCGGCA |
| JK021 (SEQ. ID. NO.:6) | PCR (−) | 42 | TGCTGCCTCGAGAAGTTGGACCTGCGGAGC GGCCTGCGCTAC |
| JK032 (SEQ. ID. NO.:7) | PCR (−) | 50 | GCAGCAAGCTTCGGACGGCATTTTTGATCA CCCGACGCACTTTGCGCCGA |
| JK033 (SEQ. ID. NO.:8) | PCR (+) | 30 | GCAGCAAGCTTCAGGGCTAGCACCAGGCGT |

[a](+) and (−) refer ro the coding DNA strand and the DNA strand complementary thereto.

genes on the chromosome (Taylor and Trotter, Bacteriol. Reviews 31 (1967), 332–344). When P1-phages propagate in bacterial cells, they pack not only viral DNA, but occasionally also a piece of the host cell genome into the virus envelope. The length of the packed bacterial DNA amounts to up to 2 minutes of the *E. coli* genome which enables the cotransduction of two remote genetic markers. If this host cell DNA enters another bacterial cell through a subsequent P1-infection, then said DNA fragment can recombine into the chromosome of this cell.

Figure 4:
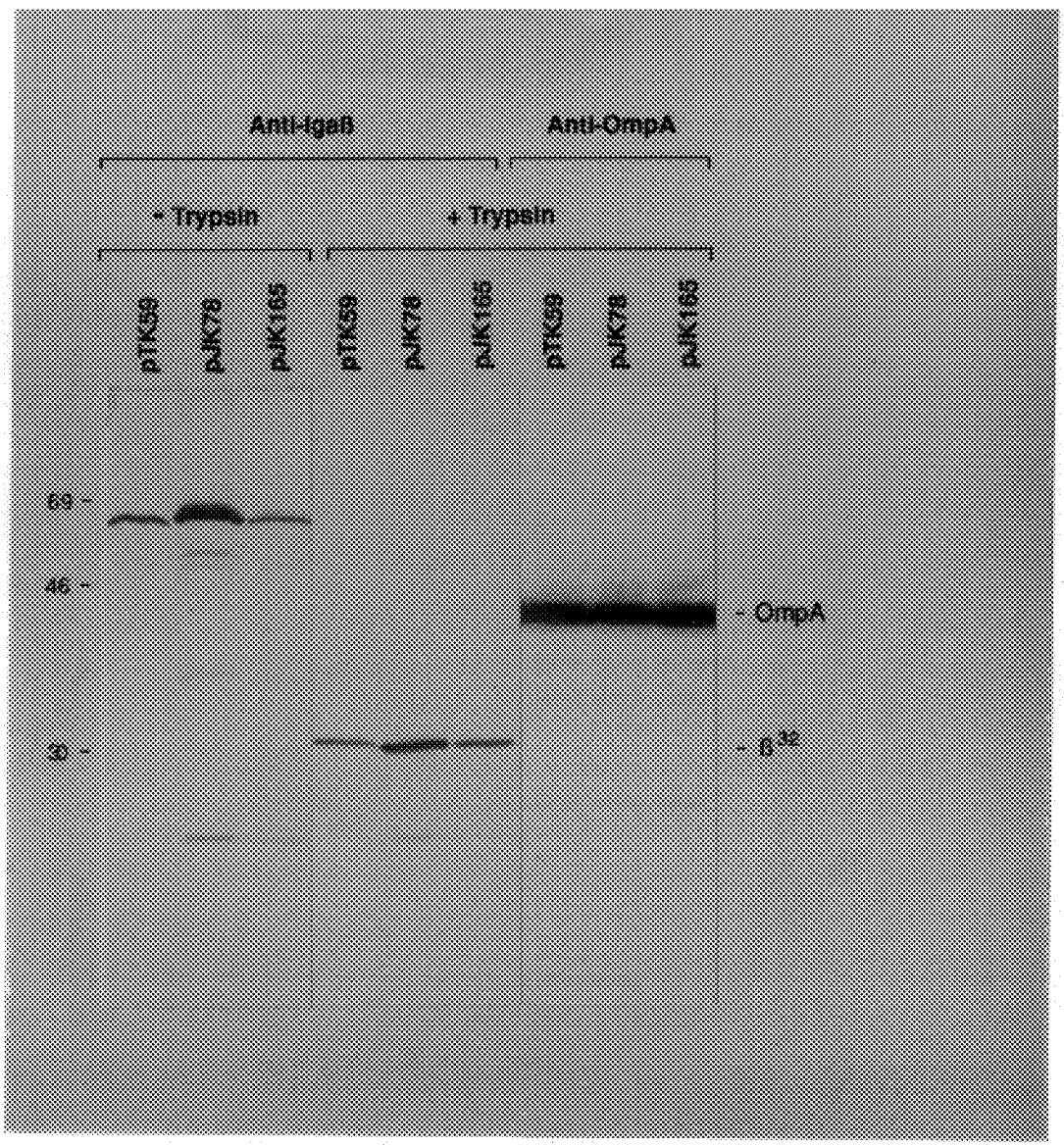
FIG. 4: Sensitivity of the surface-exposed antibody domains to trypsin in physiologically intact E. coli JK321. The immuno blot analysis of JK321 cell lysates comprising the plasmids pTK59 (lanes 1 and 4), pJK78 (lanes 2 and 5), pJK165 (lanes 3 and 6) by means of the anti-Fp42 shows the Igaβ-hybrid proteins prior to (lanes 1 to 3) and after incubation of the recombinant bacteria with protease (lanes 4 to 6). The analysis of the cell lysates by means of anti-OmpA serum (lanes 7 to 9) shows that the periplasmic carboxy terminus of the OmpA protein in the individual bacterial clones is not accessible to trypsin and thus confirms the extracellular localization of the antibody domains.

*E. coli* JCB571 (dsbA::Kan, zih12::Tn10) was chosen as the donor strain and *E. coli* UT5600 (ompT⁻) as the receptor strain to carry out P1-transduction. Following the preparation of a JCB571-specific P1-phage lysate and the infection of UT5600 cells, positive transductants having cotransduced and integrated the mutated unknown gene locus and the mutated dsbA gene into their chromosome were selected by being grown on a nutrient medium containing kanamycin and tetracyclin. Because of the localization of the dsbA (kan) gene and the transposon insertion zih12::Tn10, (tet) close to the mutation which is responsible for the VH-Igaβ stabilization and present in the *E. coli* chromosome, these two antibiotic resistances (kan and tet) were used as labels for the cotransduction. The clone so prepared (*E. coli* JK321) shows tolerance towards the VH-Igaβ fusion previously only found in *E. coli* JCB570 (wt) and JCB571 (dsbA). After transformation with the plasmids pJK78 (VL-Igaβ) and pJK165 (VH-Igaβ), the stable expression of these Igaβ fusion proteins could be shown in *E. coli* JK321 (FIG. 4). The strain JK321 also enables the simultaneous coexpression of the plasmids pJK78 (VL-Igaβ) and pJK165 (VH-Igaβ) in one bacterial cell.

EXAMPLE 2

Construction of a VH-iga$_\beta$ gene fusion and expression in *E. coli* JK321.

For the presentation of recombinant antibody fragments on the cell surface of *E. coli* JK321 it is necessary to provide the VH or VL domains with different transport signals. Hence, the antibody domains in the protein fusions prepared carry a signal peptide at the N-terminus which ensures the transport of the fusion proteins through the cytoplasmic membrane and the Igaβ-domain at the C-terminus which subsequently mediates the transport of the antibody domain through the outer membrane.

Figure 1A:
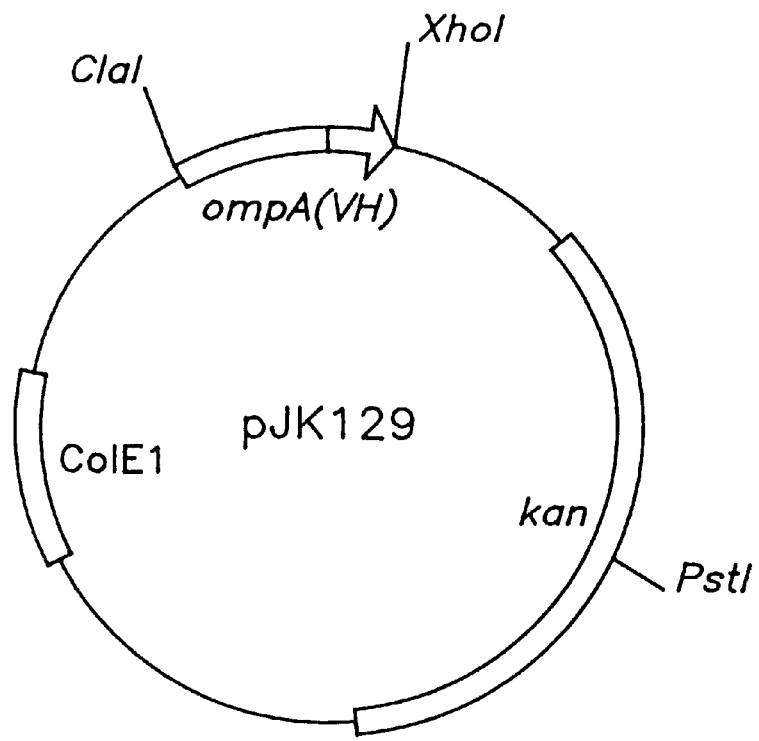
FIGS. 1A–1C Schematic representation of the strategy for constructing the VH-igaβ fusion in the plasmid pJK165. In the course of the construction of the plasmid pJK165, the VH-gene fragment at the 5' end was fused with the signal sequence of the ompA gene and at the 3'-end with the igaβ gene fragment. The DNA fragments necessary therefor were linked to each other in a three-fragment ligation. The non-coding region and the signal sequence of the ompA gene of E. coli DH5a were synthesized by PCR using the chromosomal DNA which served as a template and the oligonucleotides JK20 and JK21 (Table 1). The resulting PCR-fragment was directly inserted into the pCR1000 vector (pJK129) without being previously incubated with restriction enzymes. The VH-gene fragment was also synthesized by PCR. In this case, the corresponding cDNA served as a template and the oligonucleotides JK09 and JK17 were made use of (Table 1). The resulting PCR fragment was then incubated with Klenow polymerase, in order to fill in the sticky ends, and after restriction with EcoRI, they were inserted into the HincII/EcoRI restriction sites of the pEMBL8 vector. From the resulting plasmid pJK92 the XhoI/EcoRI VH-gene fragment was isolated and ligated together with the ClaI/XhoI ompA-gene fragment and an XhoI/EcoRI vector fragment from pTK59. The resulting pJK165 plasmid encodes an VH-igaβ fusion, whose "-10-region" of the promoter was reconstituted according to the starting plasmid pTK59 (FIG. 1C).
Figure 1B:
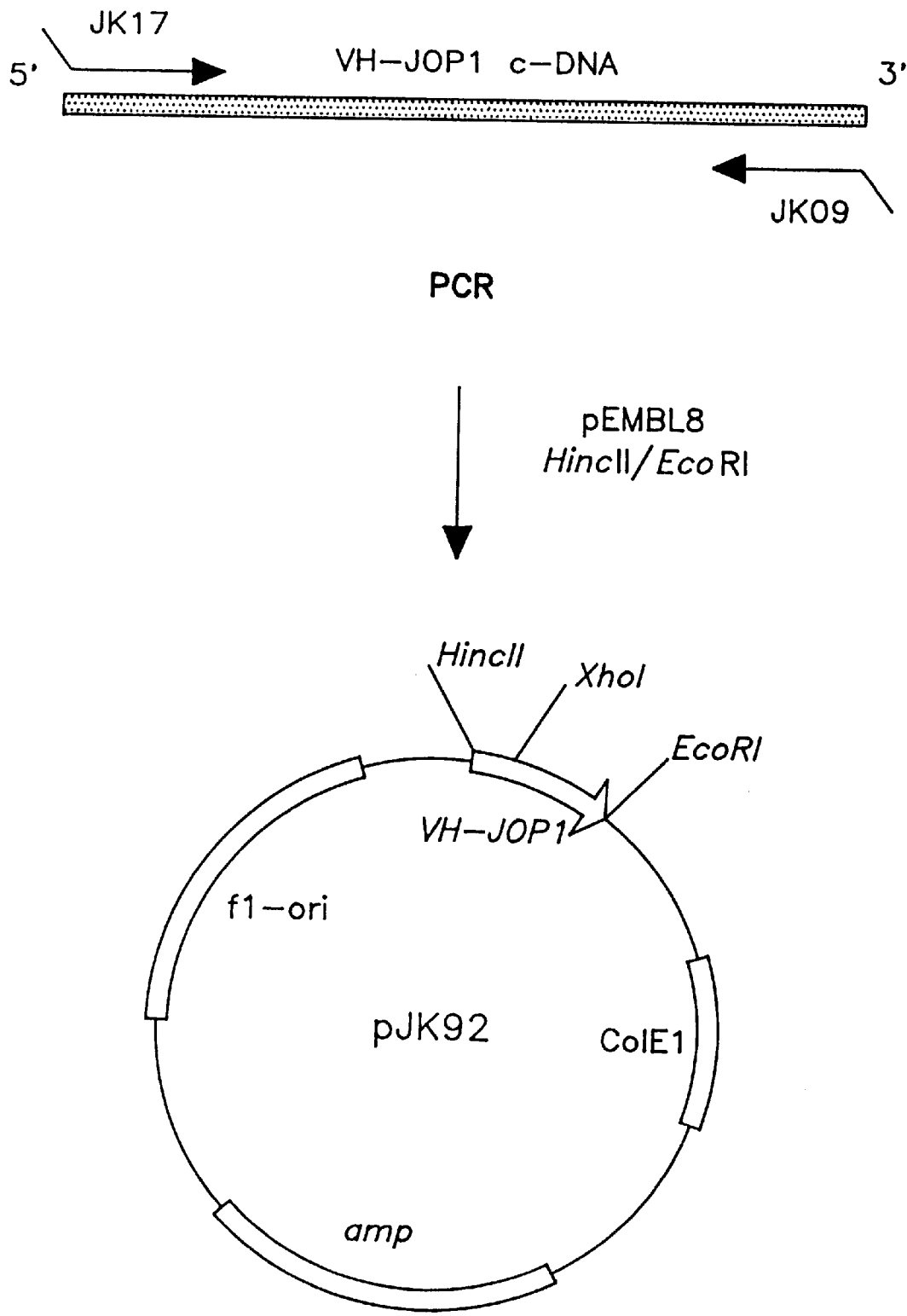
Figure 1C:
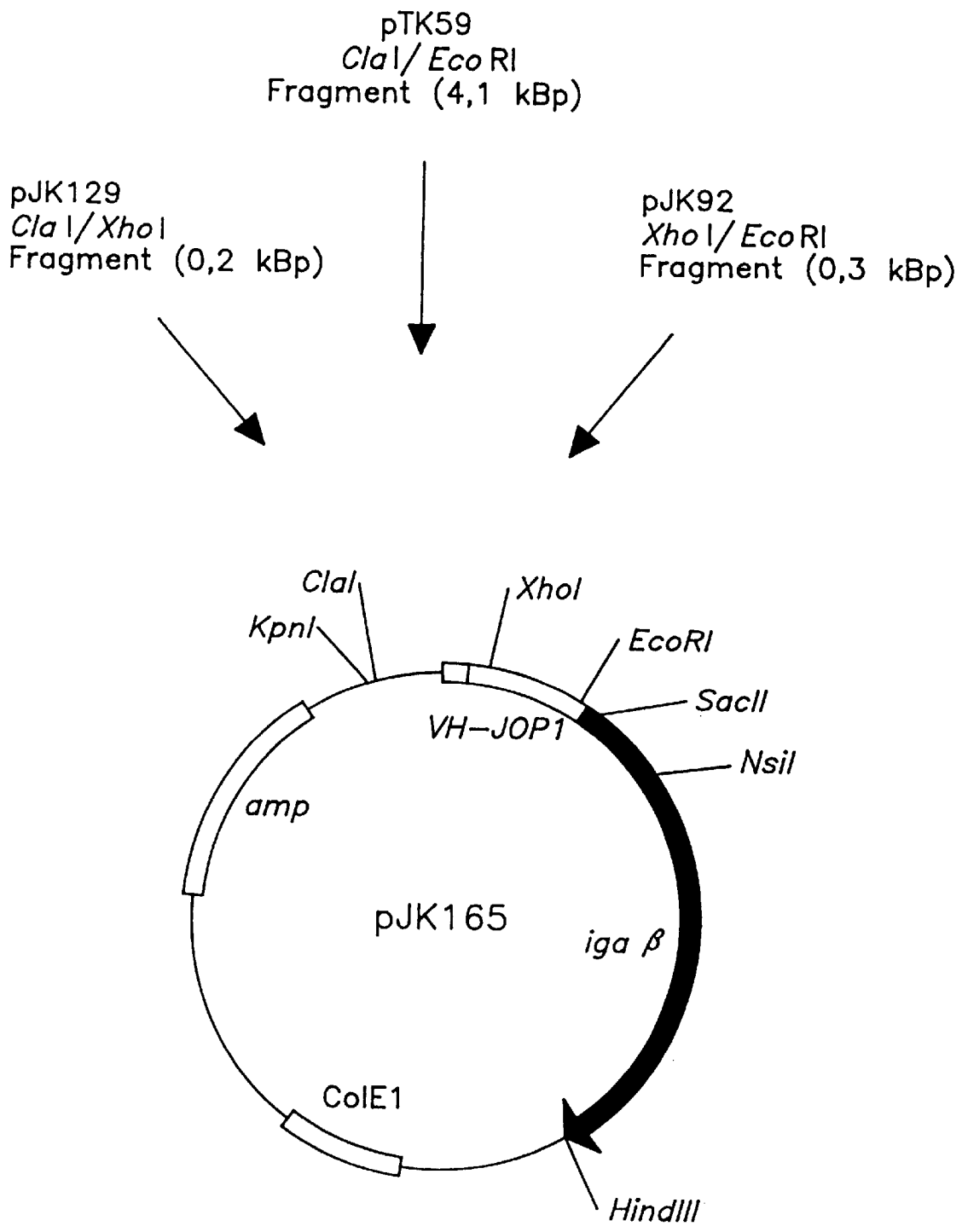

The construction of the fusion between a VH-gene fragment and igaβ occurs in the plasmid pJK165 (FIG. 1C). In the course of this construction, the region of the ompA gene of *E. coli* (Movva et al., J. Biol. Chem. 255, (1980), 27–33) which encodes the signal sequence was linked to the 5'-end of igaβ. In order to amplify the region encoding the ompA signal sequence and the non-coding region in front of it (Cole et al., Mol. Gen. Genet. 188, (1982), 472–479) by PCR, the structure of the 5'-terminal oligonucleotide JK20 (Table 1) was so chosen that the "-10-region" of the P$_{TK}$ promoter was completely reconstructed to express igaβ gene fusions after insertion of the corresponding gene fragment into the ClaI restriction site of pTK59 (Klauser et al., EMBO J. (1990), 1991–1997). The 3'-terminal oligonucleotide JK21 (Table 1) was provided with an XhoI restriction site which enabled the fusion with the 5'-end of the VH-gene fragment. For this purpose, a VH-gene fragment was amplified by PCR using the oligonucleotides JK17 and JK09 (Table 1) and fused via an XhoI-restriction site at the 5'-end with the ompA specific DNA fragment and via an EcoRI restriction site at the 3'-end with igaβ. The plasmid so formed was termed pJK165 (FIG. 1C).

After transformation of *E. coli* JK 321 with the plasmid pJK165, the recombinant bacteria were found to be highly stable. This effect does not appear in recombinant *E. coli* K12 wild type cells. In *E. coli* K12 wild type cells which carry the plasmid pJK165, the recombinant bacteria were found to be destabilized owing to a cytotoxic effect of the VH-igaβ fusion protein and the formation of mutants which no longer synthesize the VH-Igaβ fusion protein. The molecular background of these mutations is the decomposition of the plasmid pJK165 into a smaller derivative which no longer expresses the VH-igaβ fusion.

EXAMPLE 3

Construction of a VL-igaβ gene fusion and expression in *E. coli* JK321

Figure 2A:
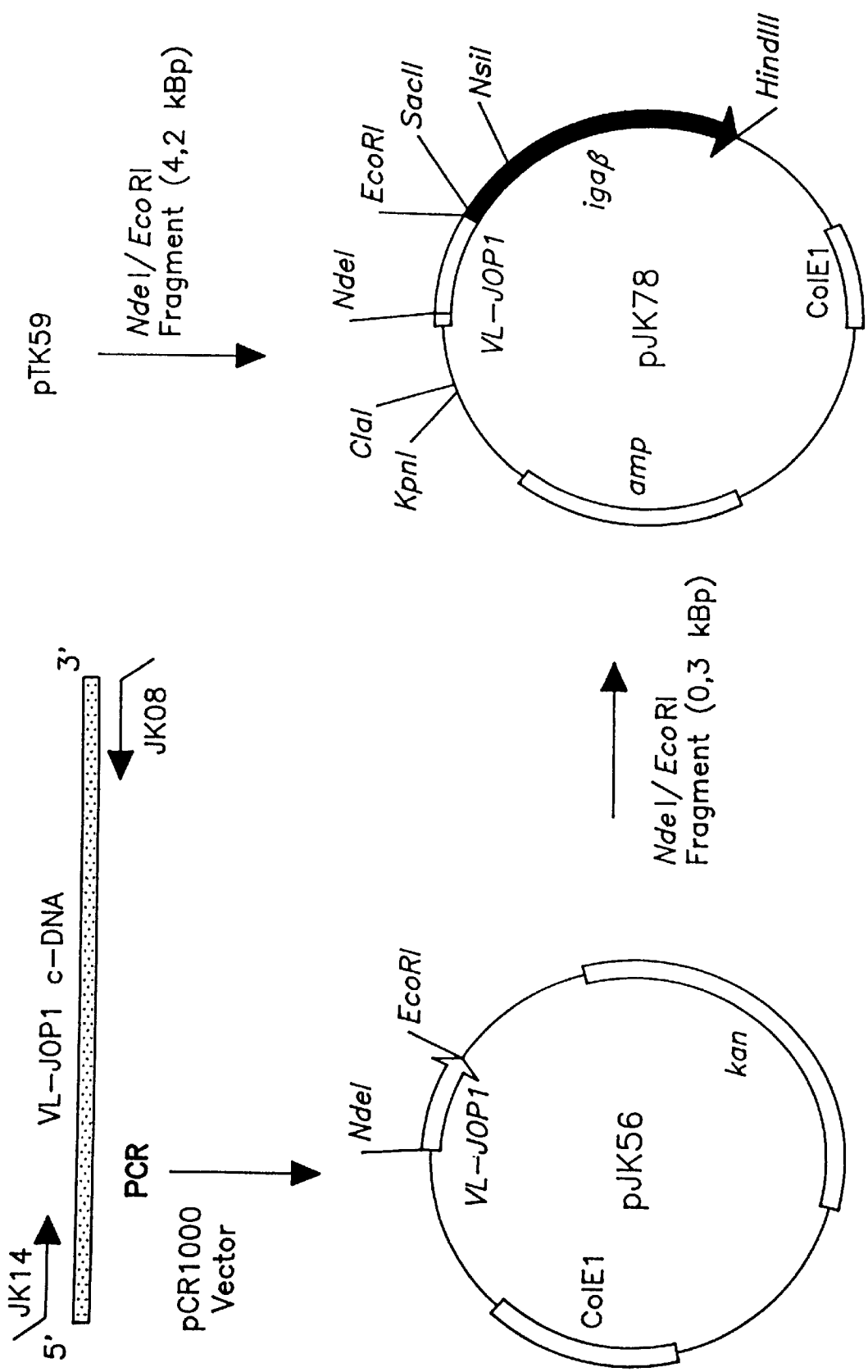
FIGS. 2A–2B Schematic representation of the strategy for constructing the VL-igaβ fusion in the plasmids pJK78 and pJK257.
Figure 2B:
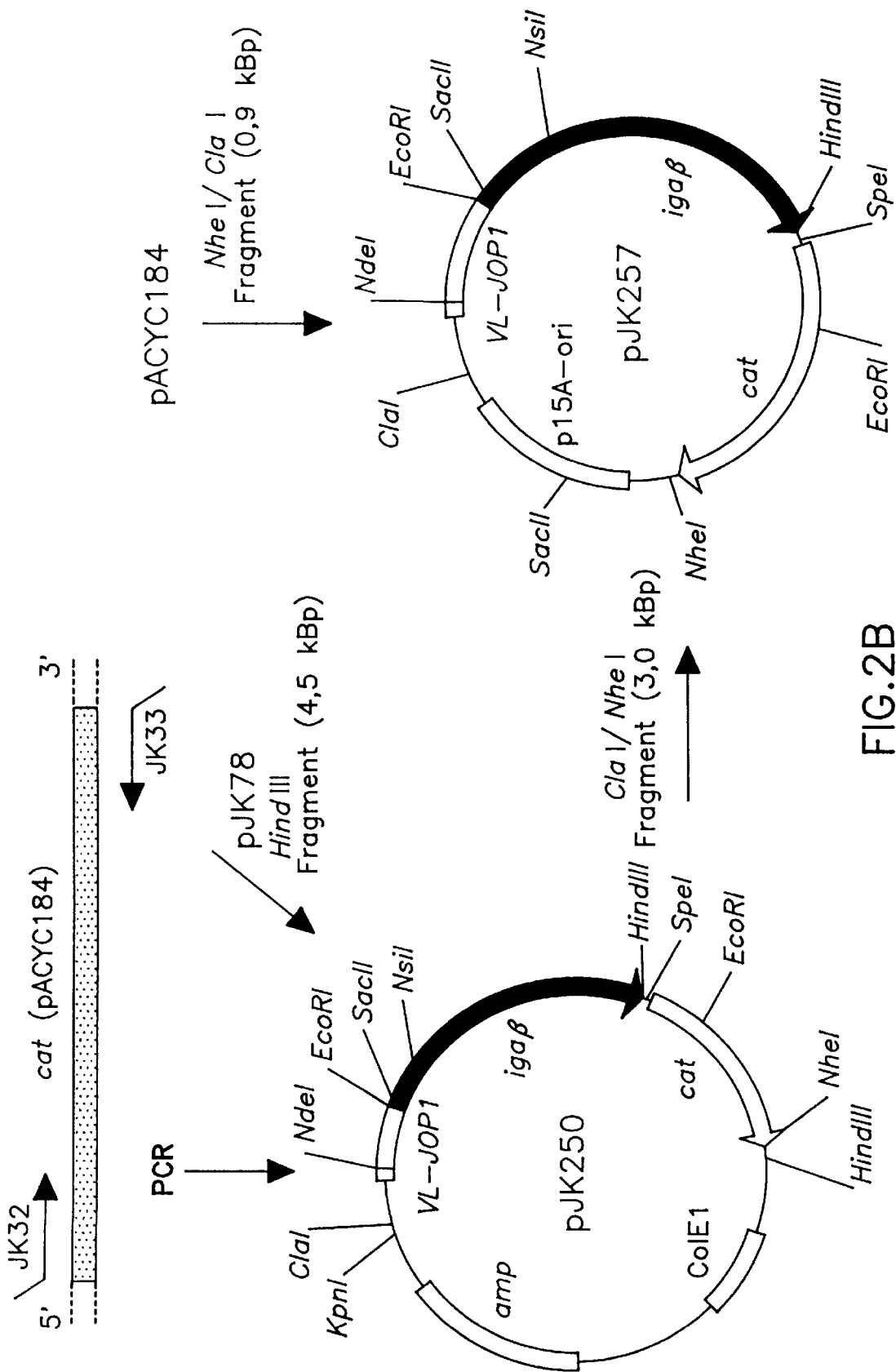
Figure 3A:
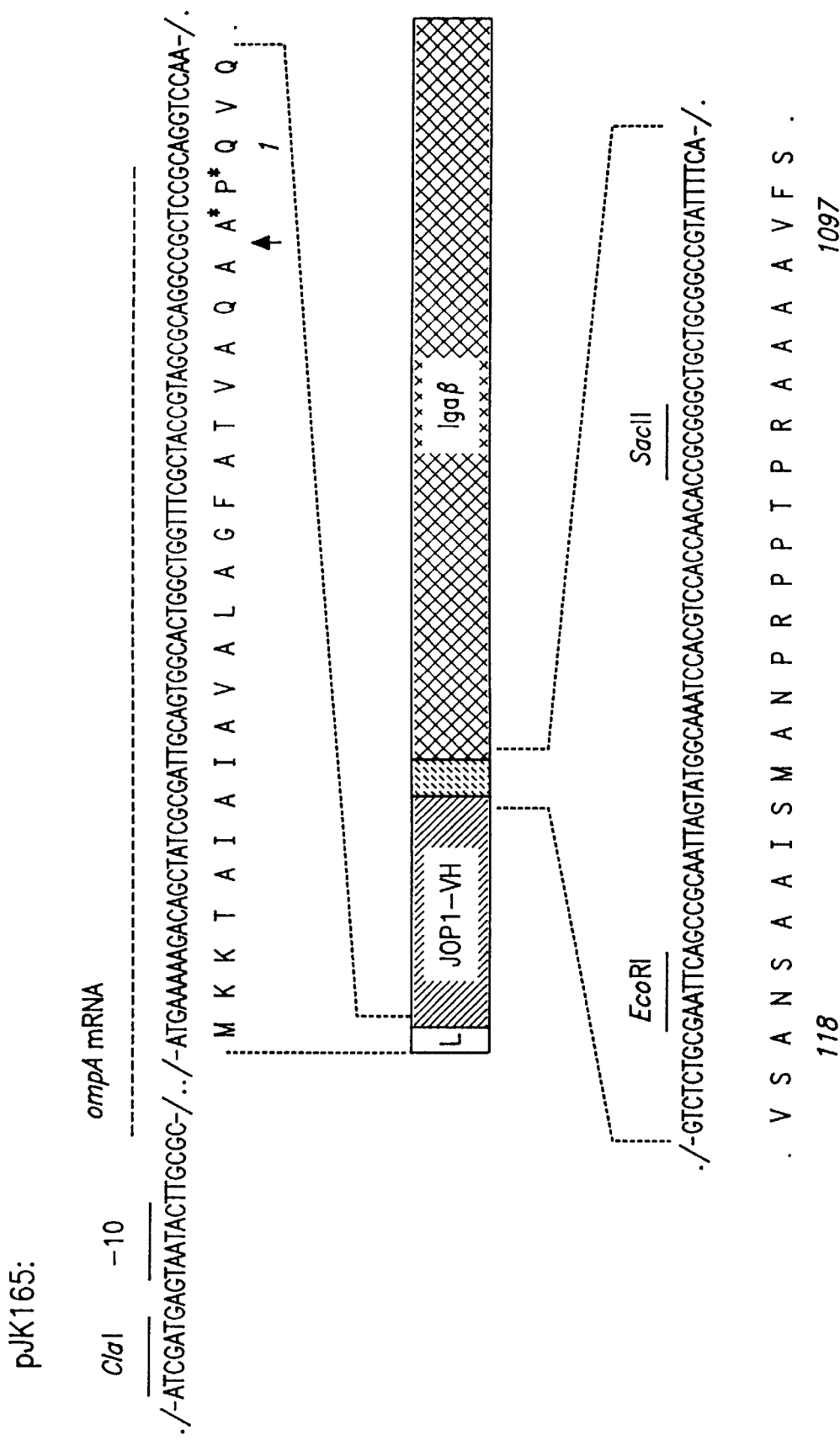
FIGS. 3A–3B: Structure of essential sequence motifs of the VH and VL-igaβ fusions used: All constructs depicted are derivatives of the plasmid pTK59 and show different important transition areas of the corresponding fusions. (i) The VH-igaβ construct pJK165 was formed by substitution of the ClaI/EcoRI fragment of pTK59 with the VH gene fragment and a DNA fragment encoding the first 204 base pairs of the E. coli ompA transcript. Thus, the VH-Igaβ fusion possesses the signal peptide of the OmpA precursor protein at its N-terminus. (ii) The VL-igaβ construct pJK78 was formed by insertion of the VL-gene fragment into the NdeI/EcoRI restriction sites of pTK59; Hence, the resulting VL-Igaβ fusion carries the CtxB signal peptide. (iii) in the plasmid pJK257, which is a VL-igaβ derivative of pJK78, the vector fragment (bla and ColEl) was replaced with the cat and p15A marker of the plasmid pACYC184, whereby the coexpression of the plasmids pJK257 and pJKl65 within one cells becomes possible. The transition areas in this VL-igaβ gene fusion are identical to those of pJK78 and therefore are not indicated separately. The restriction sites of the signal peptidase are marked with arrows. In order to ensure an efficient processing by the signal peptidase, two amino acids of the native OmpA and CtxB proteins were left at the N-terminus of the antibody domains (identified by asterisks). Numbers written in italics indicate the first and the last amino acid positions of the variable antibody domains in the Igaβ-fusions and amino acids written in bold letters denote the newly introduced restriction site of the IgA-protease (Pohlner et al., Bio/Technology 10 (1992), 799–804) SEQ ID NOS: 9, 10, 11, 12 & 13 are presented in FIG. 3A. SEQ ID NOS: 14, 15, 16, 17 & 18 are presented In FIG. 3B.
Figure 3B:
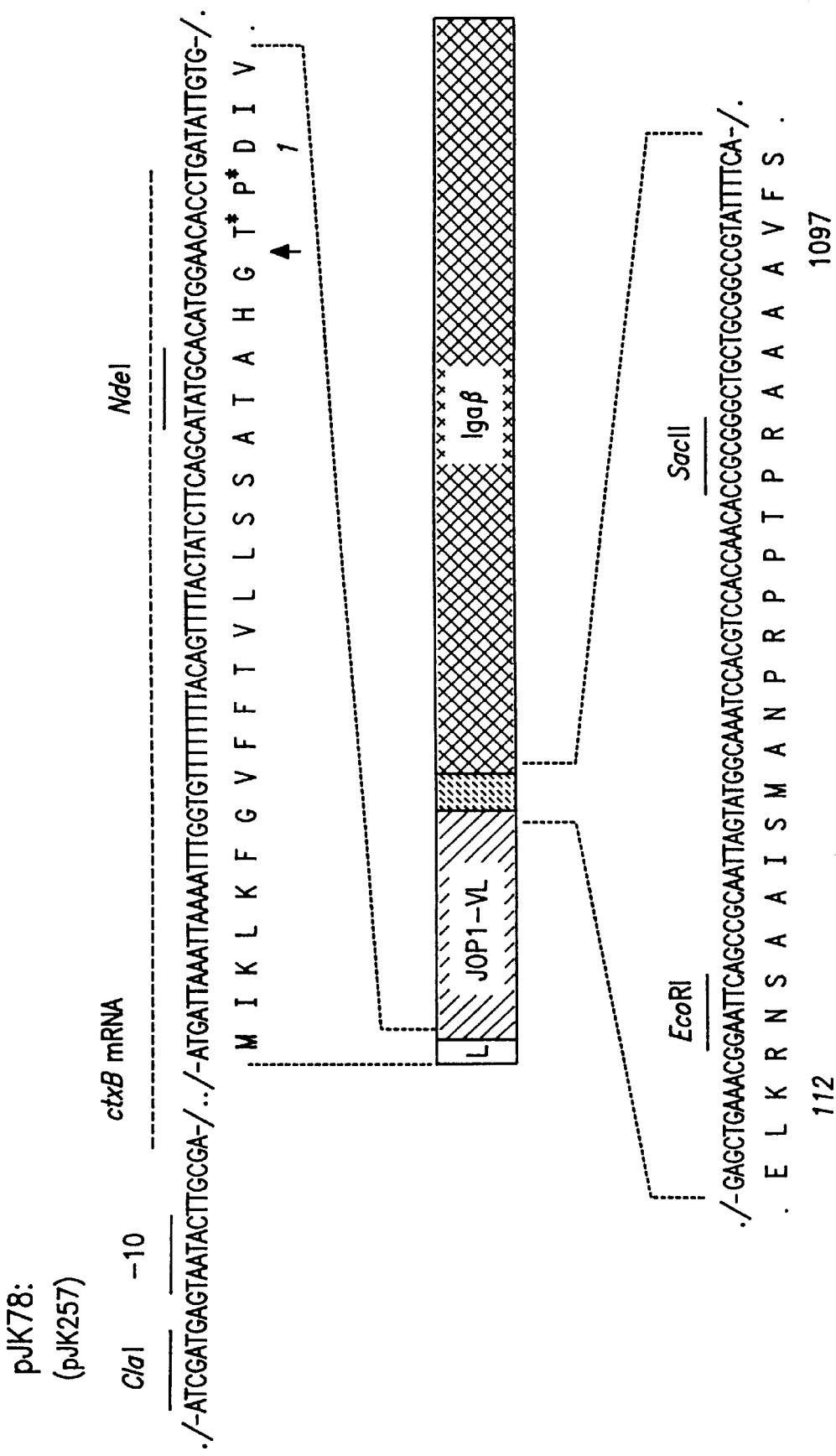

For a simultaneous surface-presentation of VH- and VL-Igaβ fusion proteins within one bacterial cell it was necessary to prepare a fusion between the VL-domain of an antibody and Igaβ, in addition to the VH-Igaβ fusion described in item 2.). The construction of a VL-igaβ fusion occurred in two steps (plasmids pJK78 and pJK257): In the first step the VL-domain was bound at its N-terminus to a signal peptide and at its C-terminus to the Igaβ domain (plasmid pJK78). The signal peptide ensures the transport of the fusion protein through the cytoplasmic membrane, and the Igaβ-domain subsequently mediates the transport for the VL-antibody domain through the outer membrane. In the second step, the ColEl-replication origin and the gene of β-lactamase (bla) in the plasmid pJK78 is exchanged for the pA15-replication origin and the gene of chloramphenicol-acetyl transferase (cat) of the cloning vector pACYC184 (Rose, Nucl. Acid Res. 16 (1978), 355) to form the plasmid pJK257. The detailed construction of the two plasmids is described in the legend to FIGS. 2a/b and FIG. 3. The use of different replication origins and resistance genes in the plasmids pJK165 and pJK257 enables the copropagation of the two plasmids within one bacterial cell.

EXAMPLE 4

The constructed *E. coli* strain JK321 enables the Igaβ-mediated exposure of variable antibody domain on the cell surface and the binding of specific antigens.

Figure 5:
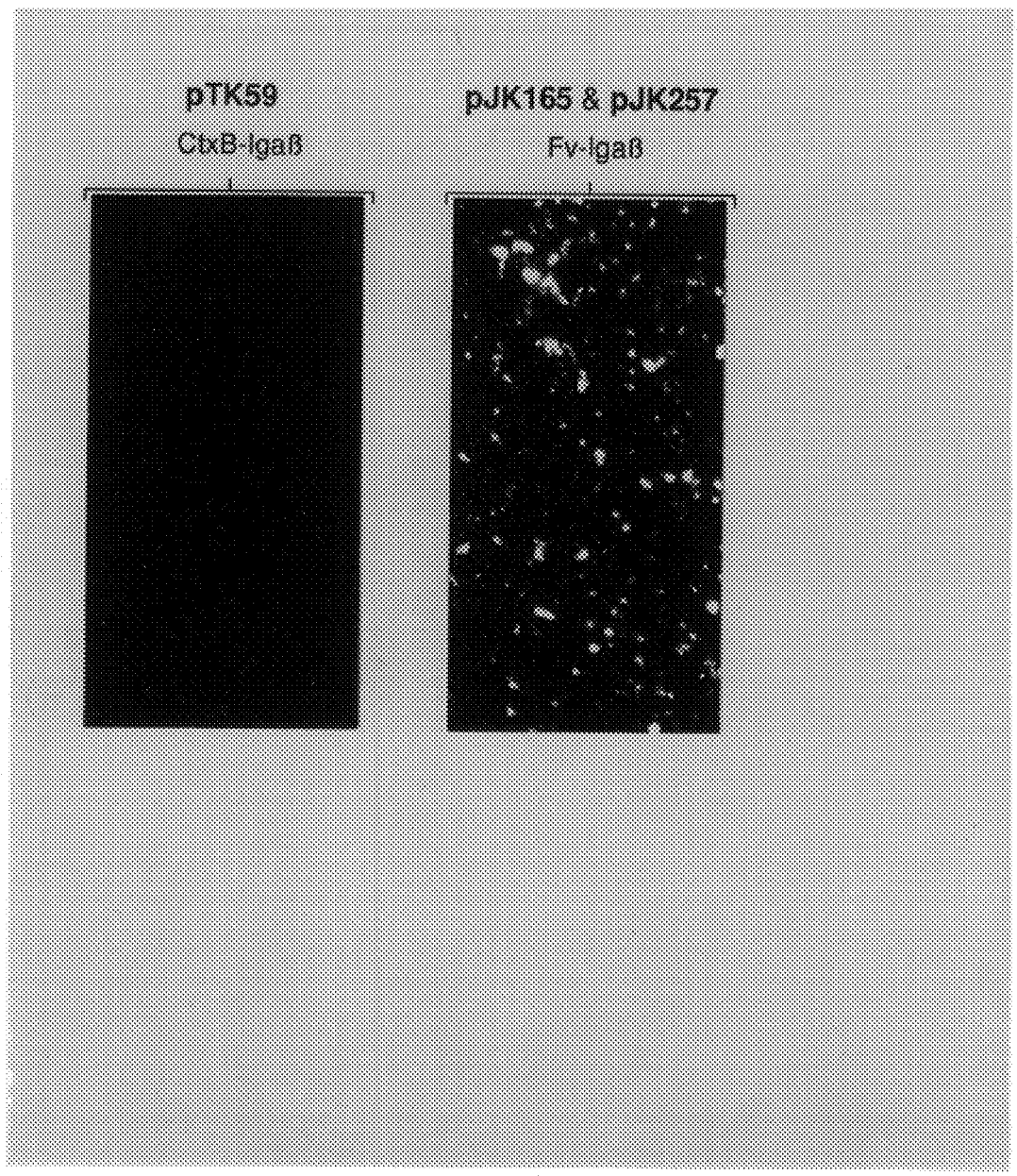
FIG. 5: Detection of a-protein on the surface of antibody-presenting E. coli JK321 by immunofluorescence-labelling.

The use of the constructed *E. coli* strain JK321 enables the presentation of antibody fragments on the cellular surface (FIGS. 4 and 5). In this process, both the production of only VH- or VL-Igaβ fusion proteins (for instance pJK165 or pJK257) and the simultaneous production of the VL and VH-igaβ fusions of two plasmids (for instance pJK165 and pJK257) is possible within one bacterial cell. In the latter case, the two fusion proteins are transported separately from each other into the outer membrane where the VL- and VH domains of the fusion proteins anneal to form a Fv-fragment. The VL- and VH-Igaβ fusions are thereby exposed on the cellular surface of *E. coli* JK321 as a Fv-Igaβ heterodimer. Recombinant *E. coli* JK321 which export heterodimer VH-/

VL-Igaβ fusion proteins to the cell surface bind the specific antigen (FIG. 5) via their immunoglobulin portions. Moreover, recombinant *E. coli* JK321 cells which coexpress the VH- and VL-Igaβ fusion proteins of two plasmids within one bacterial cell can be enriched using the specific antigen from a dilution by *E. coli* JK321 cells which export other unspecific Igaβ-fusion proteins (for instance CtxB-Igaβ, plasmid pTK59) (FIG. 7).

EXAMPLE 5

Development of a method for detecting the enriched, antibody-presenting *E. coli* JK321 cells.

After experiments to select recombinant bacteria, which present on the cellular surface antibody fragments having a defined antigen specificity, it is necessary to determine the identity of the clones enriched by means of the specific antigen. One possibility to exclusively detect *E. coli* cells that surface-present antibody fragments having a defined specificity consists in incorporating a particular genetic marker (for instance an antibiotic resistance) into the host cells that are used. Accordingly, the *E. coli* JK321 cells possess a resistance gene against the antibiotic rifampicin. To this end, a DNA fragment carrying such a resistance gene was transformed into *E. coli* JK321 cells. The DNA fragment recombined into the genome of *E. coli* JK321 and led to the expression of the rifampicin resistance. This additional quality of the *E. coli* JK321 host cells only allows recombinant *E. coli* clones that simultaneously present VL- and VH-Igaβ fusions of a defined specificity selected before the experiment to selectively grow on a rifampicin-containing medium. The recombinant control cells used for the test (for instance *E. coli* UT5600) which simultaneously surface-present VL- and VH-Igaβ fusions having a different antigen specificity are sensitive to rifampicin. The use of host cells which are resistant (JK321) or sensitive (UT5600) to rifampicin enables the unambiguous identification of the specific, antibody-presenting cells (FIG. 6).

We claim:

1. A bacterium possessing the markers fpt, ompT⁻ and dsbA⁻.

2. The bacterium according to claim 1, said bacterium further comprising a gene encoding a fusion protein comprising a carrier protein and a passenger protein.

3. The bacterium according to claim 2, wherein said gene encoding a fusion protein comprises a nucleic acid sequence encoding the Igaβ protein or a fragment of the Igaβ protein effective for secretion of said fusion protein.

4. The bacterium according to claim 3, wherein the marker fpt is present in a fragment of the genome of *E. coli* JCB571 between the markers dsbA::Kan and zih12::Tn10.

5. A method for preparing a fusion protein comprising culturing a bacterium according to claim 4 under conditions such that said fusion protein is expressed on the surface of said bacterium, and isolating said bacterium from said culture.

6. A method for preparing a fusion protein comprising culturing a bacterium according to claim 3 under conditions such that said fusion protein is expressed on the surface of said bacterium, and isolating said bacterium from said culture.

7. The bacterium according to claim 2, wherein the marker fpt is present in a fragment of the genome of *E. coli* JCB571 between the markers dsbA::Kan and zih12::Tn10.

8. A method for preparing a fusion protein comprising culturing a bacterium according to claim 2 under conditions such that said fusion protein is expressed on the surface of said bacterium, and isolating said bacterium from said culture.

9. The bacterium according to claim 1, wherein the marker fpt is present in a fragment of the genome of *E. coli* JCB571 between the markers dsbA::Kan and zih12::Tn10.

10. A method for expressing a fusion protein comprising transforming a bacterium according to claim 1 with a vector comprising a DNA fragment encoding a fusion protein.

11. The bacterium according to claim 1, wherein the passenger protein is a protein having an affinity to a binding partner, an antibody, an antigen-binding domain of an antibody, an antigen, a protein having enzymatic activity, an inhibitor, a receptor, a ligand, or a nucleic-acid binding protein.

12. The bacterium according to claim 11, wherein the marker fpt is present in a fragment of the genome of *E. coli* JCB571 between the markers dsbA::Kan and zih12::Tn10.

13. A method for identifying bacteria which stably present proteins having an affinity to a binding partner, comprising:

(a) constructing at least one vector containing at least one DNA sequence encoding a fusion protein which is made from a carrier protein and a passenger protein and can be stably presented on the surface of the bacteria according to claim 1;

(b) introducing the vector into said bacteria according to claim 1;

(c) culturing the bacteria of step (b) in such a way that the bacteria of the resulting culture stably present the fusion protein(s) on their surface;

(d) isolating bacteria which present the desired fusion protein(s) on their surface.

14. The method according to claim 13, wherein the construction of the vector in step (a) is performed using a library of DNA sequences in which the corresponding DNA-sequences encode variants of the passenger protein(s).

15. The method according to claim 13, wherein the culturing of the bacterium in step (c) is carried out under conditions under which the fusion protein or the DNA sequence encoding the fusion proteins is mutated, with the result that the bacteria of the resulting culture present variants of the fusion protein(s) on their surface.

16. The method according to claim 13, wherein the carrier protein contained in the fusion protein contains the Igaβ protein or a fragment thereof effective for secretion of the fusion protein.

17. The method according to claim 13, wherein the protein having an affinity to a binding partner is an antibody, an antigen-binding domain of an antibody, an antigen, a protein having enzymatic activity, an inhibitor, a receptor, a ligand or a nucleic-acid binding protein.

18. The method claim 13, wherein the bacteria which present the desired fusion protein on their surface are isolated by interaction with an immobilized binding partner of the passenger protein, or by interaction with a fluorescently-labeled binding partner of the passenger protein, or by interaction with a magnetic particle-bound binding partner of the passenger protein.

19. *E. coli* JK 321 (DSM 8860).

20. A gram negative bacterium which stably surface-presents at least one fusion protein comprising a carrier protein and a passenger protein and possesses the genetic markers fpt, ompT⁻, and dsbA⁻.

21. The bacterium according to claim 20, wherein the carrier protein contained in the fusion protein contains the Igaβ protein or a fragment thereof effective for secretion of the fusion protein.

22. The bacterium according to claim 20 wherein the passenger protein is a protein having an affinity to a binding partner, an antibody, an antigen-binding domain of an antibody, an antigen, a protein having enzymatic activity, an inhibitor, a receptor, a ligand or a nucleic-acid binding protein.

23. A method for preparing a bacterium for the stable expression of a cell-surface localized protein comprising transducing into a single gram-negative bacterium the genetic markers fpt, ompT⁻ and dsbA⁻.

24. The method according to claim 23, wherein the marker fpt is present in a DNA fragment obtained from the genome of *E. coli* JCB571 between the markers dsbA::Kan and zih12::Tn10.

* * * * *

```
                         SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE PRIMER"

(iii) HYPOTHETICAL: NO (iv) ANTI-SENSE: YES (xi) SEQUENCE DESCRIPTION: SEQ ID NO:1:

GCAGCAGAAT TCCGTTTCAG CTCCAGCTTG GTCCC                                       35

(2) INFORMATION FOR SEQ ID NO:2:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
 (A) DESCRIPTION: /desc = "OLIGONUCLEOTIDE P (iii) HYPOTHETICAL: NO (iv) ANTI-SENSE: YES (xi) SEQUENCE DESCRIPTION: SEQ ID NO:2:

GCAGCAGAAT TCGCAGAGAC AGTGACAGTR GTGCCTTGGC CCCA                             44
```

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE PRIMER"

(iii) HYPOTHETICAL: NO (xi) SEQUENCE DESCRIPTION: SEQ ID NO:3:

GGTTATGCAT ATGCACATGG AACACCTGAT RTTGTGATRA CCCA          44

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE PRIMER"

(iii) HYPOTHETICAL: NO (iv) ANTI-SENSE: NO (xi) SEQUENCE DESCRIPTION: SEQ ID NO:4:

GGTTATGCAT ATGCACATGG AACACCTCAG GTCCAACTTC TCGAGTCAGG          50

(2) INFORMATION FOR SEQ ID NO:5:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE PRIMER"

(iii) HYPOTHETICAL: NO (iv) ANTI-SENSE: NO (xi) SEQUENCE DESCRIPTION: SEQ ID NO:5:

GCAGCAATCG ATGAGTAATA CTTGCGCGCC AAGGGTGCTC GGCA          44

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE PRIMER"

(iii) HYPOTHETICAL: NO (iv) ANTI-SENSE: YES (xi) SEQUENCE DESCRIPTION: SEQ ID NO:6:

```
TGCTGCCTCG AGAAGTTGGA CCTGCGGAGC GGCCTGCGCT AC                        42

(2) INFORMATION FOR SEQ ID NO:7:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "OLIGONUCLEOTIDE PRIMER"

(iii) HYPOTHETICAL: NO (iv) ANTI-SENSE: YES (xi) SEQUENCE DESCRIPTION: SEQ ID NO:7:

GCAGCAAGCT TCGGACGGCA TTTTTGATCA CCCGACGCAC TTTGCGCCGA                50

(2) INFORMATION FOR SEQ ID NO:8:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "OLIGONUCLEOTIDE PRIMER"

(iii) HYPOTHETICAL: NO (iv) ANTI-SENSE: NO (xi) SEQUENCE DESCRIPTION: SEQ ID NO:8:

GCAGCAAGCT TCAGGGCTAG CACCAGGCGT                                      30

(2) INFORMATION FOR SEQ ID NO:9:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "FRAGMENT OF PLASMID pJK165"

(xi) SEQUENCE DESCRIPTION: SEQ ID NO:9:

ATCGATGAGT AATACTTGCG C                                               21

(2) INFORMATION FOR SEQ ID NO:10:

(i) SEQUENCE CHARACTERISTICS:
         (A) LENGTH: 77 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "FRAGMENT OF PLASMID pJK165"

(xi) SEQUENCE DESCRIPTION: SEQ ID NO:10:

ATGAAAAAGA CAGCTATCGC GATTGCAGTG GCACTGGCTG GTTTCGCTAC CGTAGCGCAG      60

GCCGCTCGCA GGTCCAA                                                    77
```

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Met Lys Lys Thr Ala Ile Ala Ile Ala Val Ala Leu Ala Gly Phe Ala
 1               5                  10                  15

Thr Val Ala Gln Ala Ala Pro Gln Val Gln
             20                  25
```

(2) INFORMATION FOR SEQ ID NO:12:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "FRAGMENT OF PLASMID pJK165"

(xi) SEQUENCE DESCRIPTION: SEQ ID NO:12:

```
GTCTCTGCGA ATTCAGCCGC AATTAGTATG GCAAATCCAC GTCCACCAAC ACCGCGGGCT      60

GCTGCGGCCG TATTTTCA                                                    78
```

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Val Ser Ala Asn Ser Ala Ala Ile Ser Met Ala Asn Pro Arg Pro Pro
 1               5                  10                  15

Thr Pro Arg Ala Ala Ala Ala Val Phe Ser
             20                  25
```

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "FRAGMENT OF PLASMID pJK165"

(xi) SEQUENCE DESCRIPTION: SEQ ID NO:14:

```
ATCGATGAGT AATACTTGCG A                                                21
```

-continued (2) INFORMATION FOR SEQ ID NO:15:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "FRAGMENT OF PLASMID pJK165"

(xi) SEQUENCE DESCRIPTION: SEQ ID NO:15:

```
ATGATTAAAT TAAAATTTGG TGTTTTTTTT ACAGTTTTAC TATCTTCAGC ATATGCACAT      60

GGAACACCTG ATATTGTG                                                   78
```

(2) INFORMATION FOR SEQ ID NO:16:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Ile Lys Leu Lys Phe Gly Val Phe Phe Thr Val Leu Leu Ser Ser
 1               5                  10                  15

Ala Thr Ala His Gly Thr Pro Asp Ile Val
            20                  25
```

(2) INFORMATION FOR SEQ ID NO:17:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "FRAGMENT OF PLASMID pJK165"

(xi) SEQUENCE DESCRIPTION: SEQ ID NO:17:

```
GAGCTGAAAC GGAATTCAGC CGCAATTAGT ATGGCAAATC CACGTCCACC AACACCGCGG      60

GCTGCTGCGG CCGTATTTTC A                                               81
```

(2) INFORMATION FOR SEQ ID NO:18:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Glu Leu Lys Arg Asn Ser Ala Ala Ile Ser Met Ala Asn Pro Arg Pro
 1               5                  10                  15

Pro Thr Pro Arg Ala Ala Ala Ala Val Phe Ser
            20                  25
```